US010918920B2

(12) United States Patent
Ding et al.

(10) Patent No.: US 10,918,920 B2
(45) Date of Patent: Feb. 16, 2021

(54) APPARATUS AND METHODS TO TRACK MOVEMENT OF SPORTS IMPLEMENTS

(71) Applicant: Intel Corporation, Santa Clara, CA (US)

(72) Inventors: Ke Ding, San Jose, CA (US); Lakshman Krishnamurthy, Portland, OR (US); Narayan Sundararajan, Palo Alto, CA (US); Xue Yang, Arcadia, CA (US)

(73) Assignee: Intel Corporation, Santa Clara, CA (US)

( * ) Notice: Subject to any disclaimer, the term of this patent is extended or adjusted under 35 U.S.C. 154(b) by 96 days.

(21) Appl. No.: 15/704,838

(22) Filed: Sep. 14, 2017

(65) Prior Publication Data

US 2019/0076710 A1    Mar. 14, 2019

(51) Int. Cl.
| | |
|---|---|
| *A63B 60/46* | (2015.01) |
| *A63B 24/00* | (2006.01) |
| *A63B 71/06* | (2006.01) |
| *A63B 69/00* | (2006.01) |
| *A63B 1/00* | (2006.01) |

(Continued)

(52) U.S. Cl.
CPC ............... *A63B 60/46* (2015.10); *A63B 1/00* (2013.01); *A63B 24/0006* (2013.01); *A63B 24/0021* (2013.01); *A63B 24/0062* (2013.01); *A63B 69/0015* (2013.01); *A63B 71/0622* (2013.01); *A63B 2024/0012* (2013.01); *A63B 2102/18* (2015.10); *A63B 2102/20* (2015.10); *A63B 2102/22* (2015.10); *A63B 2102/24* (2015.10); *A63B 2102/32* (2015.10); *A63B 2220/44* (2013.01); *A63B 2220/803* (2013.01);
(Continued)

(58) Field of Classification Search
CPC ... A63B 60/46; A63B 24/006; A63B 24/0021; A63B 24/0062; A63B 69/0015; A63B 69/62; A63B 2102/20; A63B 2220/44; A63B 2220/803; A63B 2220/833
See application file for complete search history.

(56) References Cited

U.S. PATENT DOCUMENTS

| | | | |
|---|---|---|---|
| 9,636,578 B1 * | 5/2017 | Ricky | A63F 13/245 3/245 |
| 2009/0298605 A1 * | 12/2009 | Wiegers | A63B 57/00 473/199 |

(Continued)

OTHER PUBLICATIONS

United States Patent and Trademark Office, "Notice of Allowance and Fee(s) Due", issued in connection with U.S. Appl. No. 15/812,746 dated Feb. 20, 2020, 7 pages.

(Continued)

*Primary Examiner* — Tramar Harper
*Assistant Examiner* — Jeffrey K Wong
(74) *Attorney, Agent, or Firm* — Hanley, Flight & Zimmerman, LLC

(57) ABSTRACT

Methods, apparatus, systems, and articles of manufacture to track movement of sports implements are disclosed herein. An example sensing unit disclosed herein is to be coupled to a sports implement. The sensing unit includes an inertial measurement unit to obtain movement data of said sports implement during a swing of said sports implement and a swing analyzer to determine a follow-through pattern of the swing of said sports implement based on the movement data.

21 Claims, 9 Drawing Sheets

(51) Int. Cl.
*A63B 102/20* (2015.01)
*A63B 102/18* (2015.01)
*A63B 102/32* (2015.01)
*A63B 102/22* (2015.01)
*A63B 102/24* (2015.01)

(52) U.S. Cl.
CPC ..... *A63B 2220/833* (2013.01); *A63B 2225/20* (2013.01); *A63B 2225/50* (2013.01)

(56) References Cited

U.S. PATENT DOCUMENTS

| | | | | |
|---|---|---|---|---|
| 2011/0065488 A1* | 3/2011 | Okamura | ............... | G06F 3/0346 463/3 |
| 2013/0102419 A1* | 4/2013 | Jeffery | ............... | G09B 19/0038 473/409 |
| 2013/0267335 A1* | 10/2013 | Boyd | ............... | A63B 69/36 473/222 |
| 2015/0018111 A1 | 1/2015 | Nadkarni et al. | | |
| 2015/0251071 A1* | 9/2015 | Steusloff | ............ | A63B 69/3632 702/141 |
| 2019/0038947 A1 | 2/2019 | Ding et al. | | |

OTHER PUBLICATIONS

United States Patent and Trademark Office, "Non-Final Office Action", issued in connection with U.S. Appl. No. 15/812,746 dated Aug. 22, 2019, 12 pages.

Intel News Byte, "Intel Technologies Unleash New Insights and Fan Experiences for Cricket at the ICC Champions Trophy 2017," [https://newsroom.intel.com/news/intel-technologies-unleash-new-insights-fan-experiences-cricket-icc-champions-trophy-2017/], dated May 30, 2017, retrieved on Jul. 3, 2017, 6 pages.

\* cited by examiner

APPARATUS AND METHODS TO TRACK MOVEMENT OF SPORTS IMPLEMENTS

FIELD OF THE DISCLOSURE

This disclosure relates generally to sports implements, and, more particularly, to apparatus and methods to track movement of sports implements.

BACKGROUND

Many sports, including cricket, are played with sports equipment or implements, such as a bat, that is swung to hit a ball or other sports implement. There are also many different types or forms of swings that a batter may use to hit a ball or other sports implement with a bat.

Figure 1:
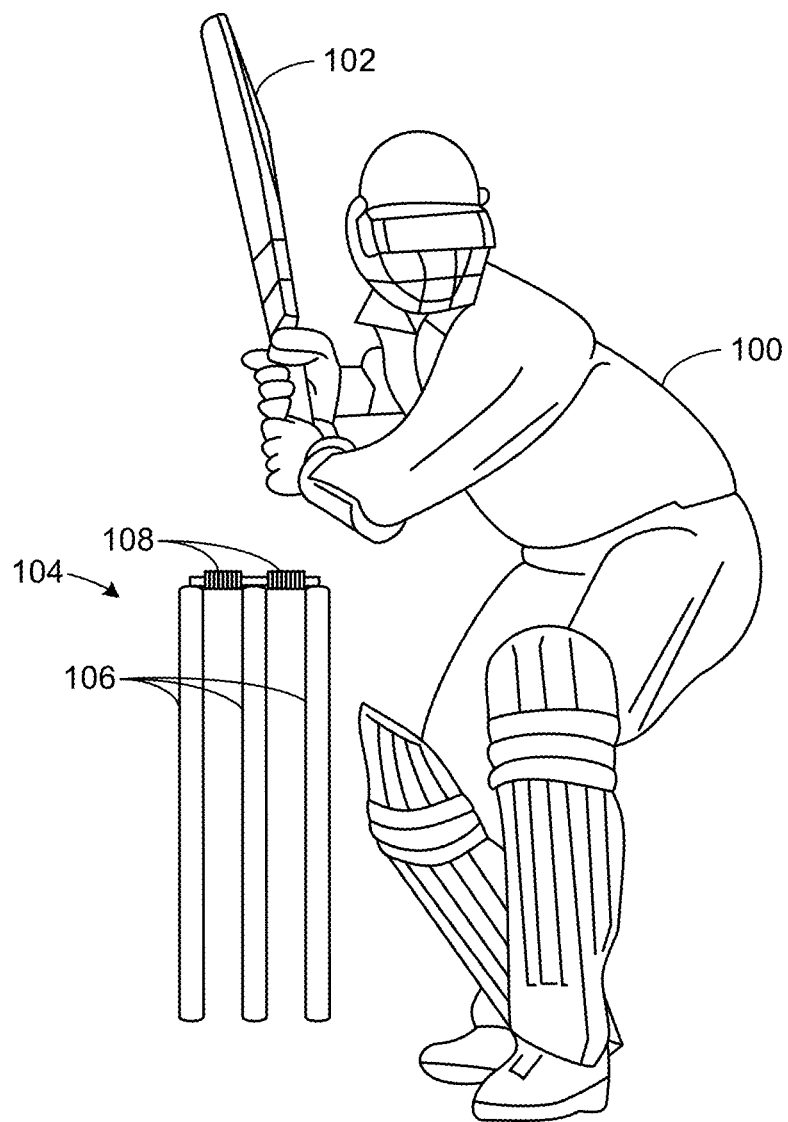
FIG. 1 illustrates an example cricket batter with an example cricket bat with which the examples disclosed herein may be implemented.

The figures are not to scale. Instead, to clarify multiple layers and regions, the thickness of the layers may be enlarged in the drawings. Wherever possible, the same reference numbers will be used throughout the drawing(s) and accompanying written description to refer to the same or like parts. As used in this patent, stating that any part (e.g., a layer, film, area, or plate) is in any way positioned on (e.g., positioned on, located on, disposed on, or formed on, etc.) another part, indicates that the referenced part is either in contact with the other part, or that the referenced part is above the other part with one or more intermediate part(s) located therebetween. Stating that any part is in contact with another part means that there is no intermediate part between the two parts.

DETAILED DESCRIPTION

Disclosed herein are example methods, apparatus, systems, and articles of manufacture for tracking movement and determining a type of follow-through pattern and/or a follow-through angle of a swing of a sports implement or equipment, namely, a bat. Many sports, including cricket, include a bat or other sports implement (e.g., a golf club, a hockey stick, etc.) that is swung to hit a ball or other sports implement (e.g., a puck, a shuttlecock, etc.). A batter or player swings the bat in a motion that can be divided into certain stages or phases, such as back lift, forward swing, and follow-through. As used herein, the "follow-through" stage or phase of a swing is defined as the period between when the bat hits the ball (or other sports implement makes contact with another sports implement) and when the bat completes its swing and comes to a rest, before being brought back down to the side of the player or dropped to the ground. As used herein, "follow-through angle" is defined as the vertical angle of the bat (or other sports implement) at the end or final position of the follow-through stage of a swing. The motion and position of a bat during the follow-through stage and/or at the follow-through angle are important indicators that can be used to determine the angular degree a batter swings the bat, the style the bat was swung, the type of shot, and/or other metrics about a batter's swing. Cricket, for example, is one of the most popular sports in the world, and there is a high demand to accurately model, measure, present and fuse batter swing metrics for live broadcast, replay, decision making assistance, data driven coaching, new types of data mining, etc. The examples disclosed herein can be used to provide accurate metrics about a batter's swing, including the follow-through pattern and/or follow-through angle of the swing.

Some known sports tracking systems, which are used in connection with soccer, use high speed cameras or infrared (IR) cameras placed around a field to capture images or motion of the sports field and a complex vision analysis program that analyzes the images to determine goal or no-goal decisions. However, these known systems are often expensive, require complicated calibration processes, and require powerful backend servers to analyze the camera data. In particular, computer vision or motion tracking systems require relatively large computational processing power to generate the desired parameters for the sport. Further, these known systems require highly complex infrastructure, such as installing cameras around the field and, in some instances, LED lights are needed in the field to serve as markers.

Unlike the known systems mentioned above, the example methods, apparatus, systems, and articles of manufacture disclosed herein provide a relatively inexpensive, low-power, and accurate way to measure different parameters of a bat swing, including metrics relating to the follow-through stage. Example sensing units are disclosed herein that can be coupled to a bat, such as a cricket bat, and determine one or more metrics of a swing, including a type or pattern of the follow-through. An example sensing unit disclosed herein includes one or more sensors, such as an accelerometer, a gyroscope, and/or a magnetometer, to obtain movement data (e.g., measurements) during the swing of the bat. A swing analyzer, which may be implemented in a low-power microprocessor in the sensing unit, analyzes the measurements from the sensors and determines one or more metrics about the swing, such as the type of follow-through pattern and/or the follow-through angle. In some examples, the sensing unit includes a transceiver to wirelessly transmit the results of the swing analysis to a remote computer or electronic device after the swing. The results may be further fused with other data, presented to the batter and/or other people (e.g., an audience), used for training purposes, etc.

FIG. 1 shows a batter 100 (commonly referred to as a batsman) with a cricket bat 102 (referred to herein as the bat 102) standing in front of a wicket 104. The wicket 104 has three stumps 106 and two bails 108 resting on top of the three stumps 106. In the game of cricket, a bowler throws a ball at the wicket 104 and the batter 100 attempts to hit the ball with the bat 102 before the ball hits the wicket 104. If the ball hits the wicket 104 and knocks off one of the bails 108, the batter 100 is considered out.

As illustrated in FIG. 1, the batter 100 typically stands sideways relative to the bowler. In this example, the batter 100 is a right-handed batter. As such, the batter 100 stands in a position where the batter's left shoulder faces toward the bowler so that the ball travels across a front of the batter 100 toward the wicket 104. The batter 100 swings the bat 102 in the area in front of the wicket 104 and attempts to hit the ball. There are many different types of swing motions that a batter may use to hit a ball. For example, the batter 100 may swing the bat 102 in a horizontal type motion, similar to swinging a baseball bat, a vertical type swing, similar to swinging a golf club, or anywhere in between.

Figure 2:
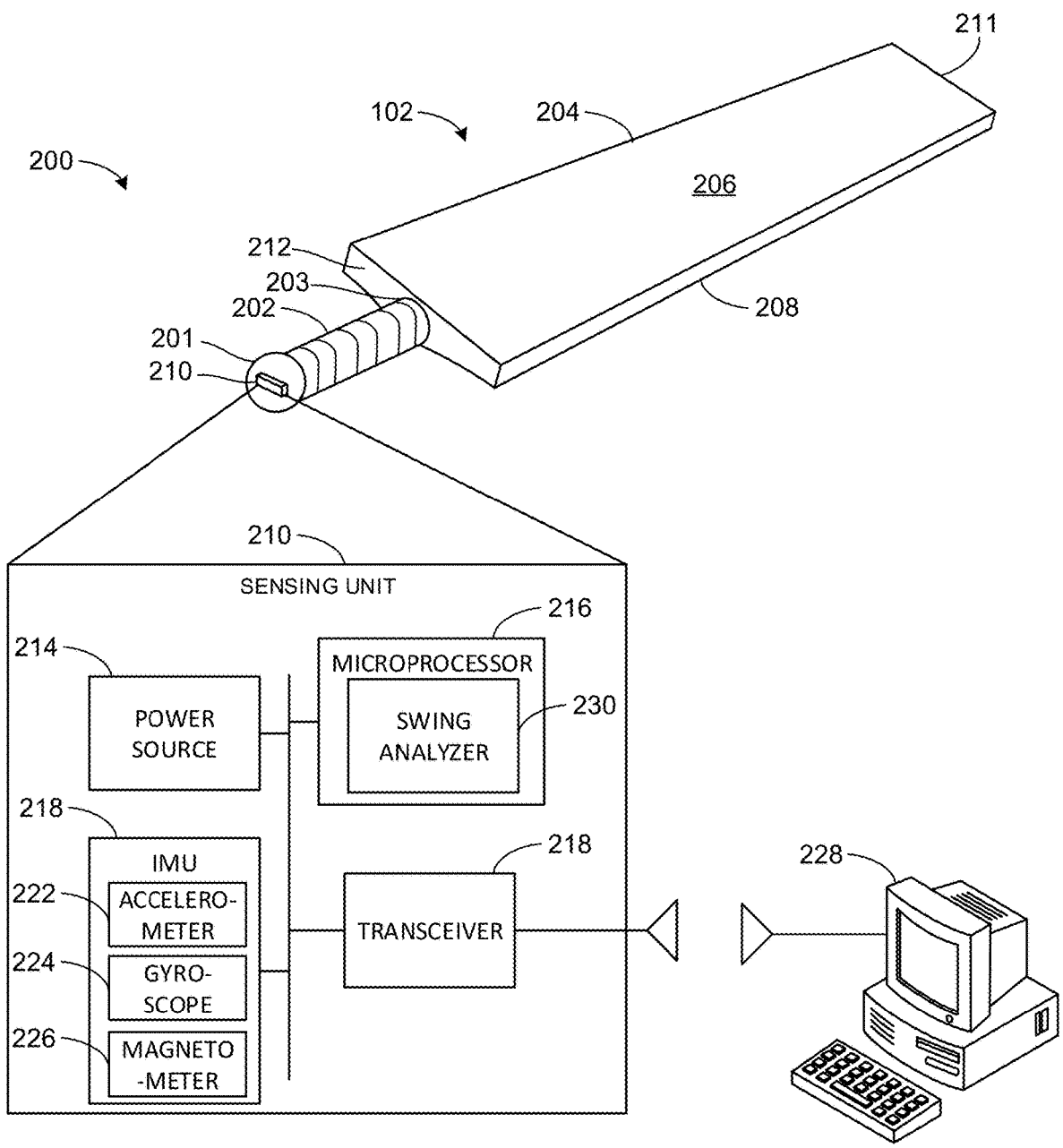
FIG. 2 illustrates an example sport tracking system, implemented in connection with the example cricket bat of FIG. 1, having an example sensing unit with an example swing analyzer and constructed in accordance with the teachings of this disclosure.

FIG. 2 illustrates an example sport tracking system 200 that may be used to track movement of and determine one or more parameters of a swing of a sports implement in accordance with one or more principles of this disclosure. The sport tracking system 200 includes a sports implement that may be swung. In this example, the sports implement is the bat 102, which has a handle 202 and a blade 204 coupled to the handle 202. The handle has a first end 201 and a second end 203, opposite the first end 201, which is coupled to the blade 204. The blade 204 has a front side 206 (commonly referred to as the string face), which is generally flat, and a back side 208 opposite the front side 206. The batter 100 (FIG. 1) holds the handle 202 of the bat 102 and attempts to hit the ball with the front side 206 of the blade 204. In the illustrated example, the first end 201 of the handle 202 is enlarged (compared to the rest of the handle 202) to help prevent a batter's hand(s) from sliding off of the handle 202. In other examples, the first end 201 of the handle 202 may not be enlarged.

To track movement of the bat 102, the example sport tracking system 200 includes an example sensing unit 210 constructed in accordance with the teachings of this disclosure. The sensing unit 210 is represented twice in FIG. 2, once as a hardware component (e.g., a chip) disposed on the cricket bat 102 and once as a block diagram. The sensing unit 210 is to be coupled to the bat 102. The sensing unit 210 may be coupled to the bat 102 via any mechanical fastener and/or chemical fastener (e.g., an adhesive). In some examples, the sensing unit 210 is to be coupled to the bat 102 at or near an end of the handle 202 of the bat 102. For example, in FIG. 2, the sensing unit 210 is coupled to the first end 201 of the handle 202. In other examples, the sensing unit 210 may be coupled to the bat 102 in another location, such as on the end of the blade 204 near the second end 203 of the handle 202, on the distal end of the blade 204, on the back side 208 of the blade 204, etc. In some examples, the sensing unit 210 may be disposed in a cavity formed in the cricket bat 102 (e.g., a cavity formed in the first end 201 of the handle 202, the distal end of the blade 204, the front side 206 of the blade 204, the back side 208 of the blade 204, the handle 202, etc.). In some such examples, a cover or plate may be disposed over the sensing unit 210 to protect the sensing unit 210.

As illustrated in the block diagram of the example sensing unit 210 in FIG. 2, the sensing unit 210 includes a power source 214, a microprocessor 216, an inertial measurement unit (IMU) 218, and a transceiver 220. The power source 214 may be implemented as, for example, a battery (e.g., a disposable or rechargeable battery) and provides electrical power to the components of the sensing unit 210. The IMU 218 includes one or more sensors that measure various parameters, referred to herein as movement data, related to movement and orientation of the cricket bat 102. In the illustrated example, the IMU 218 includes an accelerometer 222, a gyroscope 224 (sometimes referred to as a gyrometer), and a magnetometer 226. The accelerometer 22 measures acceleration (or rate of change of velocity), the gyroscope 224 measures angular speed, and the magnetometer 226 measures magnetism, which may be used to determine an orientation/direction of the cricket bat 102. In other examples, the IMU 218 may include fewer or more sensors, including additional ones of the same sensors or different sensors.

The microprocessor 216 processes and analyzes the movement data from the IMU 218, as disclosed in further detail herein, and the transceiver 220 transmits the results of the analysis to a remote electronic device 228. The microprocessor 216 is a type of processor or central processing unit that is relatively small and may have low power consumption. In other examples, other types of processors or central processing units may be used. In the illustrated example, the electronic device 228 is depicted as a personal computer. However, the electronic device 228 may be implemented as any type of electronic device such as a laptop computer, a cell phone (e.g., a smart phone), a television, a tablet, etc. that may further process, display, and/or otherwise present the results of the swing analysis. Further, in some examples, the swing results may be transmitted to multiple electronic devices. The electronic device 228 may be located outside of the cricket playing field, for example. The transceiver 220 includes a transmitter and a receiver, such that the sensing unit 210 can communicate with the electronic device 228. The transceiver 220 may be, for example, a Bluetooth® transceiver. In other examples, the transceiver 220 may be implemented by other wireless technologies, such as a low band radio transceiver. In some examples, the sensing unit 210 may communicate with the electronic device 228 over a network, such as the Internet. In other examples, the sensing unit 210 may only include a transmitter and not a receiver, such that the sensing unit 210 can only output information but not receive information.

In the illustrated example, the sport tracking system 200 includes a swing analyzer 230 that determines one or more metrics about a swing of the bat 102 based on measurements from the IMU 218. The swing analyzer 230 is disclosed in further detail in connection with FIG. 4. In the illustrated example of FIG. 2, the swing analyzer 230 is implemented in the microprocessor 216 of the sensing unit 210. The swing analyzer 230 may be, for example, a program or application executed by the microprocessor 216. Thus, in some examples, the swing analysis results are determined in the sensing unit 210 and transmitted to the electronic device 228. In other examples, the swing analyzer 230 may be implemented in the electronic device 228 (e.g., by a processor of the electronic device 228). In such an example, the movement data from the IMU 218 may be transmitted to the electronic device 228, which may then analyze the movement data and determine the metric(s) about the swing.

While in the illustrated example of FIG. 1 the components of the sensing unit 210 are depicted as being included in a common package or unit, in other examples, one or more of the parts or components of the sensing unit 210 may be separated from the other part(s) and connected via any wired or wireless connection. For example, the power source 214 may be coupled to another part of the bat 102 (e.g., in the handle 202) and electrically coupled to the IMU 218, the microprocessor 216, and/or the transceiver 220, which may be disposed in other locations on the bat 102. Also, while the example sport tracking system 200, the example sensing unit 210, and the example swing analyzer 230 are described in connection with the cricket bat 102 for analyzing a swing of the bat 102, the example methods, apparatus, systems, and articles of manufacture disclosed herein can likewise be implemented with any other sports implement that is swung, such as a baseball bat, a golf club, a hockey stick, a tennis racket, a badminton racket, etc., to strike another sports implement, such as baseball, a golf ball, a hockey puck, a tennis ball, a shuttlecock, etc., to analyze the swing in accordance with the principles of this disclosure.

Figure 3:
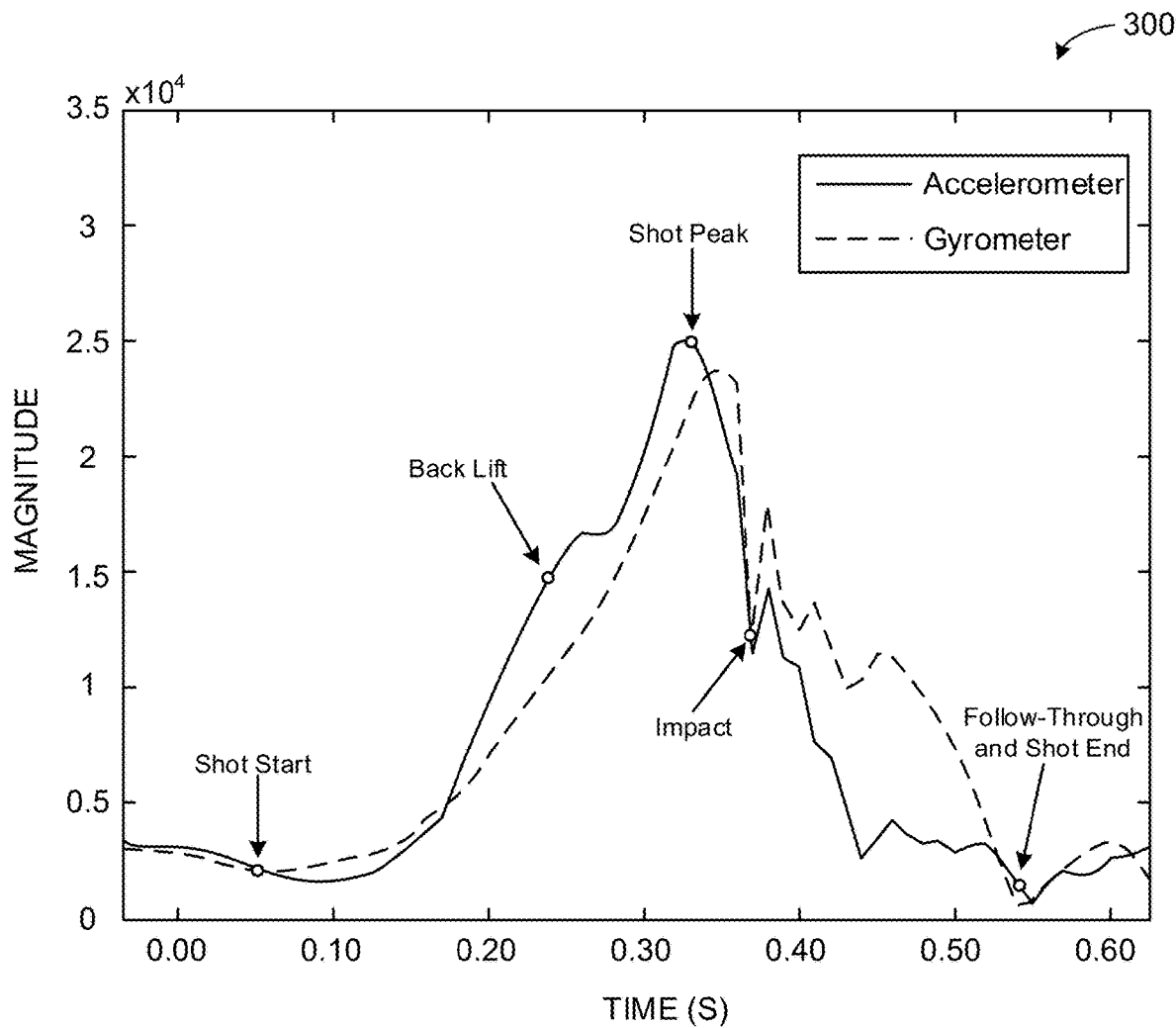
FIG. 3 illustrates an example graph showing example accelerometer and gyroscope measurements obtained by an example inertial measurement unit (IMU) of the example sensing unit of FIG. 2 during a swing of the example cricket bat.

FIG. 3 illustrates an example graph 300 showing measurements that may be obtained by the accelerometer 222 and the gyroscope 224 during an example swing of the bat 102. The Y axis of graph 300 represents magnitude and the X axis of the graph 300 represents time (in seconds (s)). Various points of the swing are labeled in the graph 300. As illustrated, at the shot start point, the magnitudes of the accelerometer 222 and the gyroscope 224 increase as the batter 100 (FIG. 1) lifts the cricket bat 102 backward (e.g., to "wind up"). The back lift or wind up phase occurs between the shot start point and the back lift point, which represents the maximum or peak position behind the batter 100 before the batter 100 begins to swing the bat 102 forward to hit the ball. The shot peak point represents the maximum magnitude in acceleration. The bat 102 makes contact with the ball at the impact point, at which point the magnitudes of the accelerometer 222 and the gyroscope 224 continue to decrease. After the impact point, the bat 102 continues to move through the follow-through stage, which ends at the follow-through and shot end point. The follow-through and shot end point represents the follow-through angle where the bat 102 finally stops. Then, batter 100 lowers the bat 102. These points and stages of the swing may be identified by the swing analyzer 230, based on the measurement data from the IMU 218, and used to determine various metrics about the swing, as disclosed in further detail herein.

In the illustrated example, the time from the shot start point to the follow-through and shot end point is about 0.5 s. In other examples, a swing may occur over a longer or shorter period of time. In some examples, the accelerometer 222 and the gyroscope 224 take measurements at a frequency of about 100 Hertz (Hz). In other examples, measurements may be obtained at a higher or lower frequency.

Figure 4:
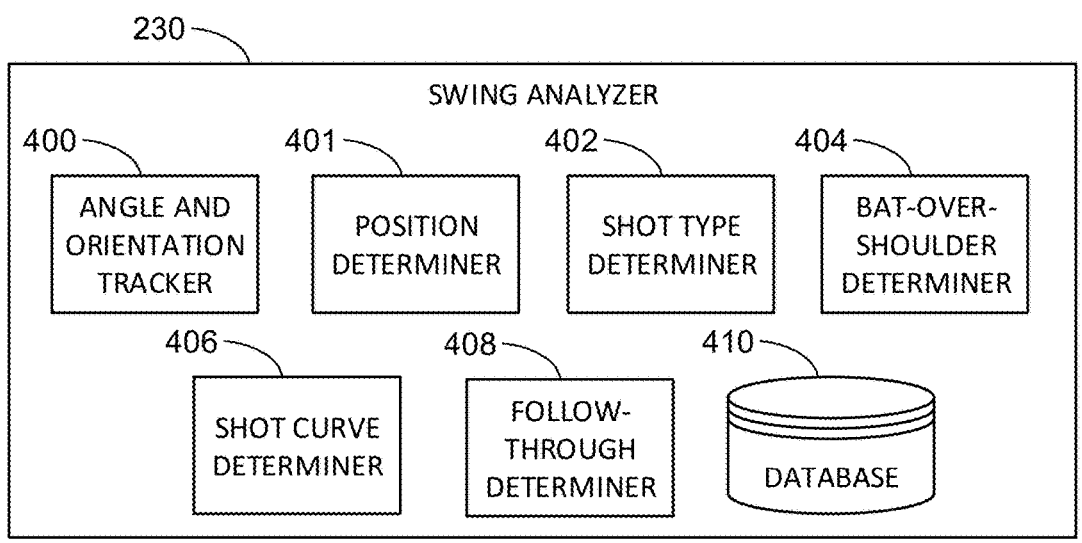
FIG. 4 is a block diagram of the example swing analyzer of FIG. 2.

FIG. 4 is a block diagram of the example swing analyzer 230, which may be implemented in the microprocessor 216 (FIG. 2) of the sensing unit 210 on the bat 102. In the illustrated example, the swing analyzer 230 includes an angle and orientation tracker 400, a position determiner 401, a shot type determiner 402, a bat-over-shoulder determiner 404, a shot curve determiner 406, a follow-through determiner 408, and a database 410. The shot type determiner 402, the bat-over-shoulder determiner 404, and the shot curve determiner 406 determine or calculate one or more metrics relating the motion and/or position of the bat 102 during the swing, and the follow-through determiner 408 determines the type of follow-through pattern and/or the follow-through angle based on or more of the metric(s), as disclosed in further detail herein. In some examples, the follow-through determiner 408 selects a follow-through pattern from a plurality of predefined patterns. For example, there may be nine established follow-through patterns. Based on the one or more metrics calculated by the other blocks, the follow-through determiner 408 can identify with accuracy the type of follow-through pattern performed by the batsman.

Figure 5:
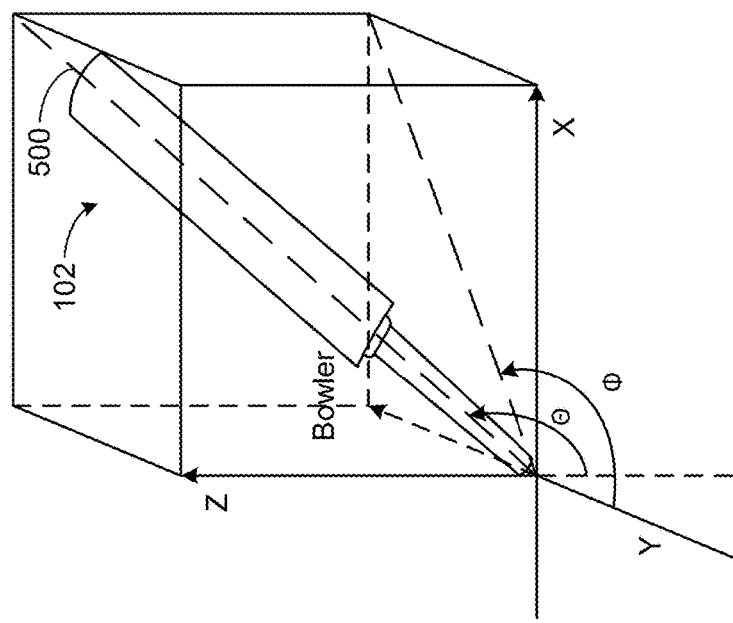
FIG. 5 illustrates an example reference frame for defining angles of orientation and movement of the example cricket bat of FIG. 2.

Before describing the details of the swing analyzer 230, an example XYZ reference frame is illustrated in FIG. 5 that is used to define the orientation and movement of the bat 102 in the disclosed examples. As illustrated in FIG. 5, the X and Y axes are horizontal axes that form a horizontal plane and the Z axis is the vertical axis perpendicular to the X, Y axes. In this example, the Y axis points toward the bowler. Assuming the batter 100 is right handed and the batter's left shoulder is facing toward the bowler during a swing, the batter's body would be facing along the X axis. As illustrated in FIG. 5, the orientation of the bat 102 defines a bat vector 500 in the XYZ reference frame. The bat vector 500 can be defined by the longitudinal axis of the bat 102, for example.

As illustrated in FIG. 5, a vertical angle θ of the bat 102 is the angle measured between the bat vector 500 and the Z axis. The vertical angle θ has a range of 0° to 180°. In this example, a vertical angle θ of 0° means the bat 102 is pointing vertically downward, and a vertical angle θ of 180° means pointing vertically upward. If the bat 102 is rotated through the 180° angle, the vertical angle θ decreases from 180° back to 0°.

Further, in the illustrated example, a horizontal angle φ of the bat 102 is the angle of the bat vector 500 in the XY plane (i.e., the reflection of the bat vector 500 on the XY plane) relative to the Y axis. The horizontal angle φ is measured as 0° to 180° in the positive X direction (in the position shown in FIG. 5) and −0° to −180° in the negative X direction (on the opposite side of the YZ plane).

Figure 6A:
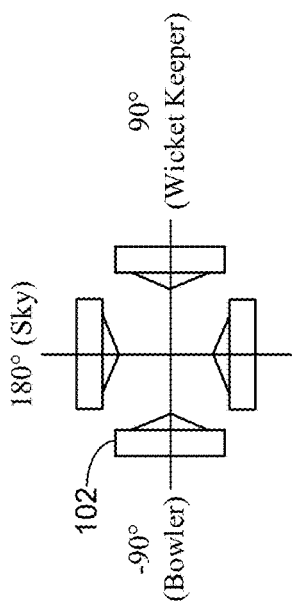
FIGS. 6A, 6B, and 6C illustrate example reference frames for determining a face angle of the example cricket bat of FIG. 2.
Figure 6B:
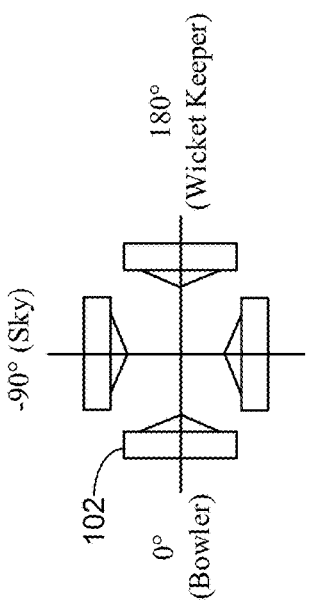
Figure 6C:
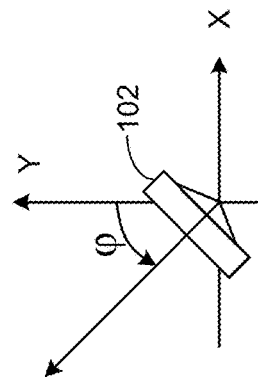

FIGS. 6A-6C illustrate reference frames for determining a face angle φ (which may be referred to as a rotational angle) of the bat 102, which represents the angle of the front side 206 (the face) of the blade 204. The angle definition is based on the type of shot and the stage or phase of the swing. For example, FIG. 6A shows the face angle φ definition for the bat 102 (labeled once in FIG. 6A) during the back lift phase of the swing (i.e., between bat start point to the back lift point) for either a horizontal shot or a vertical shot (disclosed in further detail in connection with FIGS. 7A and 7B). In some examples, to calculate the face angle φ for the bat 102 during the back lift phase (as shown in FIG. 6A), the bat 102 is put into vector [0, −1, 0] (i.e., pointing backward along the Y axis), the bat 102 is rotated to the position given by the face angle φ, the bat 102 is rotated around the X axis by (90°−vertical angle) degrees, and then the bat 102 is rotated around the Z axis (horizontal) degrees. FIG. 6B shows the face angle φ definition for the bat 102 (labeled once in FIG. 6B) from the back lift point to the follow-through end point for a horizontal shot. In some examples, the face angle φ for this phase of the swing for a horizontal shot is calculated the same as the back lift phase disclosed above in connection with FIG. 6A. FIG. 6C shows the face angle φ definition for the bat 102 from the back lift point to the follow-through end point for a vertical shot. In FIG. 6C, the face angle φ is 0° facing the bowler, the face angle φ is positive in the negative X direction, and the face angle φ is negative in the positive X direction. In some examples, to calculate the face angle φ for the bat 102 during this phase for a vertical shot (as shown in FIG. 6C), the bat 102 is put into vector [0, 0, −1] (i.e., pointing vertically downward along the Z axis, the bat 102 is rotated to the position given by the face angle φ, the bat 102 is rotated around the Y axis by −(horizontal angle) degrees, and then the bat 102 is rotated around the X axis −(vertical angle) degrees.

Referring back to FIG. 4, the angle and orientation tracker 400 of the swing analyzer 230 determines the orientation, including the vertical angle θ, the horizontal angle 9, and the face angle φ (using the reference frames defined in FIGS. 5-6C), of the bat 102 throughout a swing or a portion of a swing based on the movement data (measurements) from the sensors of the IMU 218. The angle and orientation tracker 400 may condition the signals or data from the IMU 218, such as filtering, analog-to-digital conversion, etc. In some examples, the angle and orientation tracker 400 includes a 9 degree-of-free (DOF) filter to calculate the angles using the measurements from the accelerometer 222, the gyroscope 224, and the magnetometer 226.

In some examples, the position determiner 401 determines or identifies the various key points (positions) and/or stages between the points during the swing and the angle(s) of the bat at or during the key points and/or the stages based on the angle and/or orientation data from the angle and orientation tracker 400. The key points may include the bat or shot start point, the back lift point, the impact point, and/or the follow-through and shot end point. In other examples, the bat motion may be divided into other key points and/or stages between the points. The position determiner 401 may identify the key points and/or stages based on certain changes in the vertical, horizontal, and/or face angle(s), for example. Further, the position determiner 401 may identify the angles at the key points and/or during the different stages. The angle and orientation tracker 400 and/or the position determiner 401 may also determine other metrics about the swing of the bat 102 based on the movement data from the IMU 218, such as the location of the bat 102 at the key points and/or during the different stages of the swing, the velocity and/or acceleration of the bat 102 at the key points and/or during the different stages, the maximum and/or average bat velocities during the swing, the time-to-impact (which is the time between the shot start point and the impact point, and/or whether there was impact (contact with the ball) or not.

Figure 7A:
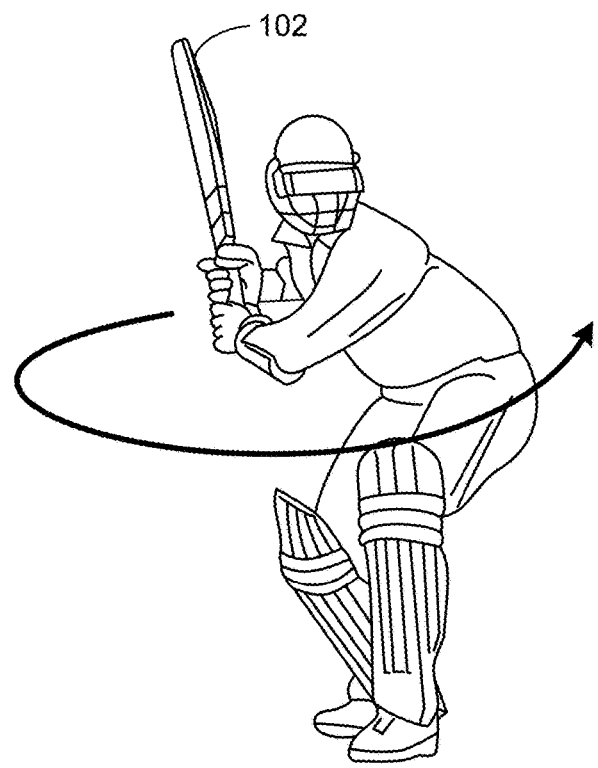
FIG. 7A illustrates an example motion path of the example cricket bat of FIG. 2 for a horizontal type shot.
Figure 7B:
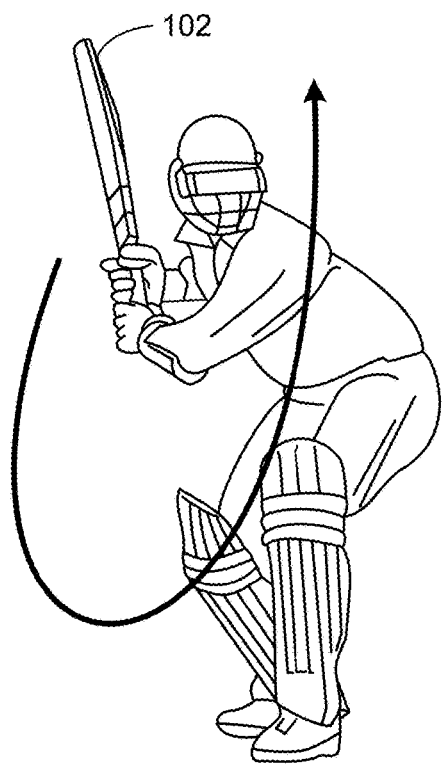
FIG. 7B illustrates an example motion path of the example cricket bat of FIG. 2 for a vertical type shot.

One metric or parameter that may be used to determine the type of follow-through pattern and/or the follow-through angle is whether the swing is a horizontal shot or a vertical shot. In particular, a cricket swing can be categorized as a horizontal shot or a vertical shot. FIG. 7A shows an example motion path of the bat 102 during a horizontal type shot, and FIG. 7B shows an example motion path of the bat 102 during a vertical type shot. In the horizontal type shot of FIG. 7A, the cricket bat 102 remains more horizontal and there is less change in the vertical angle of the bat 102 during the swing. On the other hand, in the vertical type shot of FIG. 7B, there is greater change in the vertical angle of the bat 102 and less change in the horizontal angle during the swing.

The shot type determiner 402 of the swing analyzer 230 determines whether the swing is a horizontal shot or a vertical shot. In some examples, the shot type determiner 402 determines whether the swing is a horizontal shot or a vertical shot based on the change(s) in vertical angle θ and/or horizontal angle φ during the swing. For example, the shot type determiner 402 may analyze the horizontal angle component of the swing and the vertical angle component of the swing (as determined by the angle and orientation tracker 400) and determine which component is the dominant or primary component. For instance, if the swing results in a vertical angle change that is relatively large compared to the horizontal angle change, then the swing is considered a vertical shot. As mentioned above, a vertical type shot typically has a significant change in the vertical angle and only a small change in the horizontal angle. However, if the swing results in a horizontal angle change that is relatively large compared to the vertical angle change, then the swing is considered a horizontal shot.

As another example, the shot type determiner 402 may determine whether the swing is a horizontal shot or a vertical shot based on the follow-through angle, which is the vertical angle θ of the bat 102 at the end of the follow-through stage. For example the shot type determiner 402 may identify the position where the horizontal angle φ reverses, which indicates the swing is over and the batter 100 is bringing the bat 102 back around. In some examples, the shot type determiner 402 identifies the vertical angle θ at this point and compares it to a threshold. If the vertical angle θ at the end position does not meet the threshold (e.g., is below the threshold), the shot type determiner 402 may determine the swing is horizontal shot. However, if the vertical angle θ does meet the threshold (e.g., is at or above the threshold), the shot type determiner 402 may determine the swing is a vertical shot. Therefore, in some examples, the shot type determiner 402 may only analyze the vertical angle θ to determine the shot type.

As another example, the shot type determiner 402 may compare the change in vertical angle θ during the full swing or a portion of the swing to a threshold. If the vertical angle change does not meet the threshold (e.g., is below the threshold), the shot type determiner 402 may determine the swing is horizontal shot. However, if the vertical angle change meets the threshold (e.g., is at or above he threshold), the shot type determiner 402 may determine the swing is a vertical shot. In other examples, the shot type determiner 402 may determine whether the swing is a horizontal shot or a vertical shot using other techniques.

Figure 8:
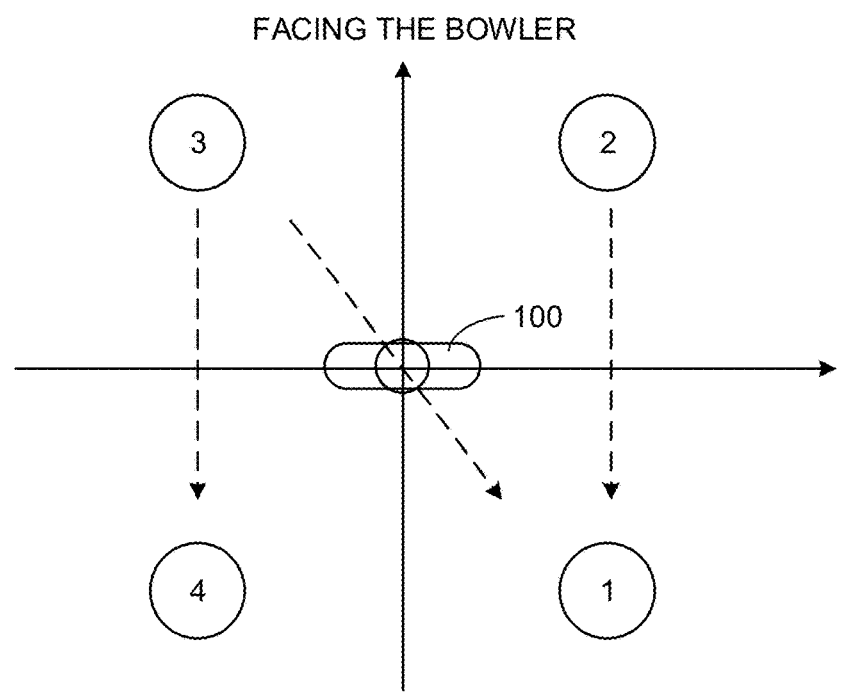
FIG. 8 is an example schematic that may be used to determine whether the example cricket bat of FIG. 2 traveled over a batter's shoulder during a swing.

Another metric or parameter that may be used to determine the type of follow-through pattern and/or the follow-through angle is whether the bat 102 was swung, during the follow-through stage, over the shoulder of the batter 100. This metric or parameter is determined by the bat-over-shoulder determiner 404 of the swing analyzer 230. Because the vertical angle θ is defined between 0° and 180°, it is important to determine whether the bat 102 is over the batter's shoulder or not when determining the follow-through angle and/or other metrics about the follow-through of the swing. If the bat 102 is over the shoulder, for example, then the follow-through angle may be calculated by: 360°− the original vertical angle at the end of the follow-through stage. FIG. 8 shows an example schematic used to illustrate how the bat-over-shoulder determiner 404 may determine whether the bat 102 was swung over the batter's shoulder. In FIG. 8, the batter 100 is facing the bowler in the direction of the Y axis, which may be the batter's body position during the follow-through stage. The XY plane is divided into four quadrants: Quadrant 1, Quadrant 2, Quadrant 3, and Quadrant 4. The bat-over-shoulder determiner 404 may determine which Quadrant the bat 102 is in based on the horizontal angle φ (determined by the angle and orientation tracker 400). For example, Quadrant 1 represents a horizontal angle φ of 0° to 90°, Quadrant 2 represents a horizontal angle φ of 90° to 180°, Quadrant 3 represent a horizontal angle φ of 0° to −90°, and Quadrant 4 represent a horizontal angle 4 of −90° to −180°. The bat-over-shoulder determiner 404 determines whether the bat 102 traveled over the shoulder depending on the movement of the bat 102 through Quadrants 1, 2, 3, and/or 4 during the follow-through stage.

For example, a swing typically starts with the bat 102 in Quadrant 1, and the bat 102 usually contacts the ball at around the intersection of Quadrants 1 and 2 (e.g., in front of the batter 100). During the follow-through stage, the bat 102 is sometimes swung into Quadrant 3 (or sometimes through Quadrant 2 to Quadrant 3). Then, the cricket bat 102 may travel from Quadrant 3 into Quadrant 1 (over the right shoulder of the batter 100) or from Quadrant 3 into Quadrant 4 (over the left shoulder of the batter 100). As indicated by the arrows between Quadrant 3 and Quadrant 1 and Quadrant 4, this movement indicates the cricket bat 102 has been swung over the batter's shoulder. As another example, the cricket bat 102 may be swung into Quadrant 2 after or during impact. Then, during the follow-through stage, the bat 102 is sometimes swung from Quadrant 2 back to Quadrant 1 (over the right shoulder of the batter 100). Thus, the bat-over-shoulder determiner 404 determines whether the bat 102 traveled over the shoulder during the follow-through stage depending on the movement of the bat 102 through Quadrants 1, 2, 3 and/or 4.

Another metric or parameter that may be used to determine the type of follow-through pattern and/or the follow-through angle is the profile or curve of the vertical angle θ during the swing. FIGS. 9A, 9B, 9C, and 9D illustrate example graphs of vertical angle θ, horizontal angle φ, and face angle 9 calculated by the angle and orientation tracker 400 for different types of shots. In each of the graphs, the Y axis represents degrees and the X axis represents time (in seconds). The shot start point, back lift point, shot peak point, impact point, and follow-through and shot end point are labeled in each of the graphs (which may be identified by the position determiner 401). The shot curve determiner 406 of FIG. 4 determines whether the vertical angle θ follows an 'N' type curve or an 'M' type curve based on the shape of the vertical angle θ line. In some examples, the shot curve determiner 406 of FIG. 4 determines whether the curve is an 'N' type or an 'M' type based on the number of peaks (crests) and valleys (i.e., local maximums and local minimums) in the vertical angle θ after the impact point but before the magnitudes of the accelerometer 222 and the gyroscope 224 are less than a threshold (e.g., 0.2). In some examples, an 'N' type curve means the vertical angle θ includes one peak and one valley after the impact point, while an 'M' type curve means the vertical angel θ includes two or more peaks and on more valleys after the impact point. The number of peaks and valleys are different for different types of follow-through patterns. This metric may be used to determine the follow-through pattern of the swing, as disclosed in further detail herein.

Figure 9A:
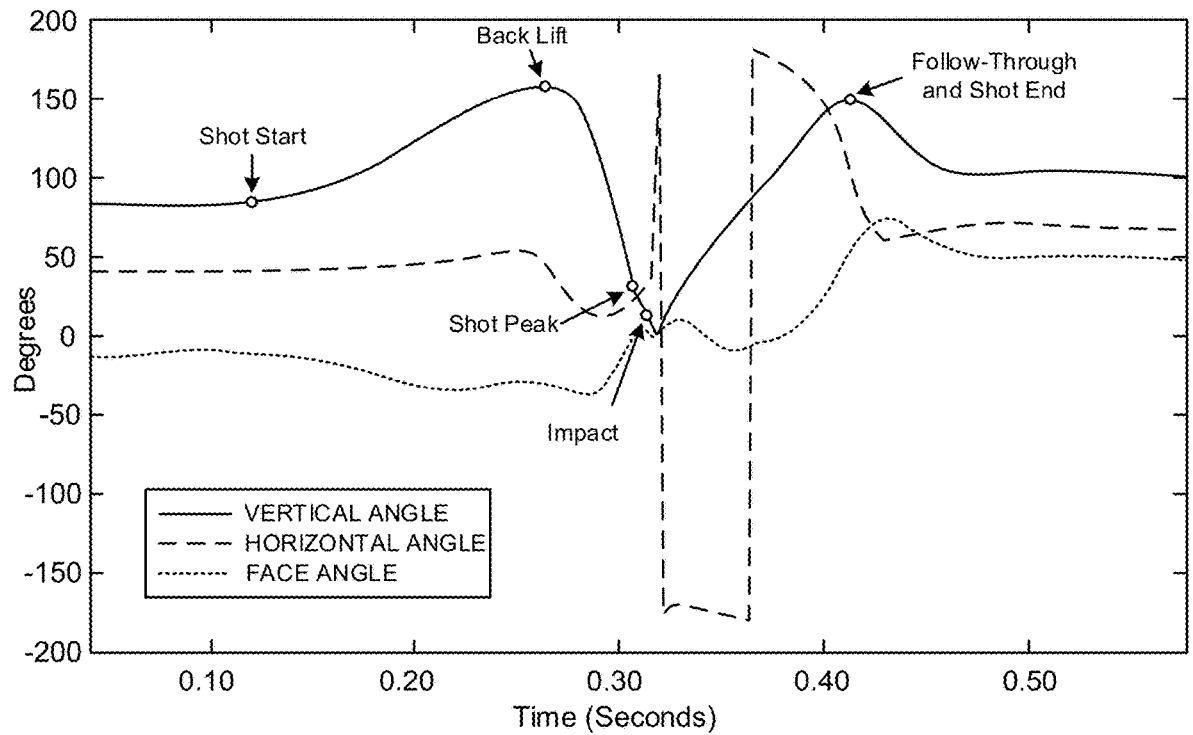
FIGS. 9A, 9B, 9C, and 9D illustrate example graphs of vertical angle, horizontal angle, and face angle during example swings that may be determined by the example swing analyzer of FIG. 2.

FIG. 9A is an example of an 'N' type curve for a vertical shot. If the curve is an 'N' type, the follow-through end point is the maximum position of the vertical angle θ. As can be seen by the vertical angle θ line, at the shot start point, the batter 100 rotates the bat 102 backwards. In other words, the bat 102 is rotated and lifted upward in the reverse direction, which produces a position change in the vertical angle θ. The back lift point is the peak of the wind up, at which point the batter 100 then swings the bat 102 down toward the ground (decreasing vertical angle θ) to the shot peak and the impact point where the ball is hit. After the impact point, the batter 100 continues to swing the bat 102 upward, which is considered the follow-through stage. The follow-through stage ends at the follow-through and shot end point, which is the maximum vertical angle θ after the impact. In this example, the vertical angle θ during the follow-through does not pass 180. Instead, the bat 102 stops or comes to a rest before 180° vertical. As can been seen in FIG. 9A, the vertical angle θ measurements form one valley and one peak during after the impact point. Therefore, the shot curve determiner 406 may determine the vertical angle θ follows an 'N' type curve based on the number of peaks and valleys in the vertical angle θ.

Figure 9B:
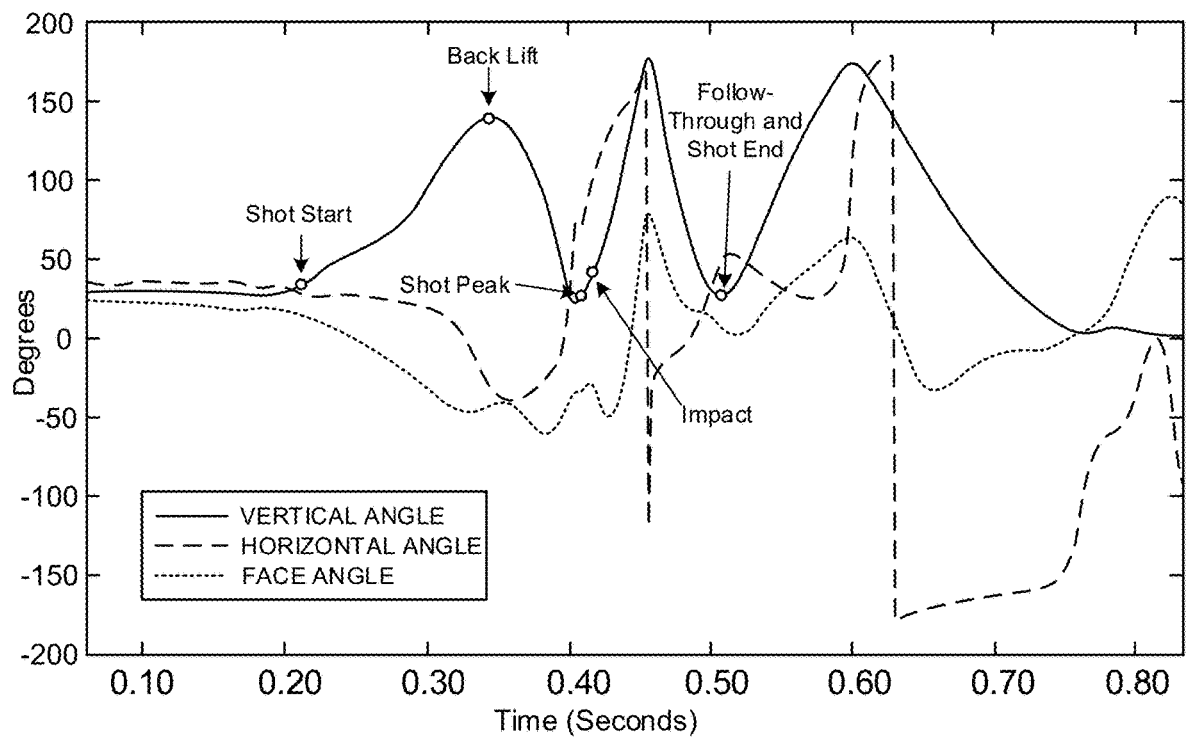

FIG. 9B, on the other hand, is an example of an 'M' type curve for a vertical shot where the bat 102 is swung passed 180° vertical during the follow-through stage. As mentioned above, the vertical angle θ is measured relative to the Z axis from 0° to 180°. After the shot peak and impact point, the bat 102 continues to rotate upward and passes the 180° vertical position, at which point the vertical angle θ then decreases from 180°. Then, once the follow-through stage ends, the bat 102 is moved back through the 180° vertical position and back to the ground as the batter 100 lowers the bat 102. This motion through the 180° vertical position in the follow-through and then back through the 180° vertical position as the bat 102 is brought back down is what generates the 'M' shape curve or profile in the vertical angle line. As can be seen in FIG. 9B, the vertical angle θ measurements form two peaks and one valley during after the impact point. This type of curve or profile is identified by the shot curve determiner 406 as an 'M' type curve.

For an 'M' type curve, such as the graph in FIG. 9B, the follow-through end point is the valley of the M shape, and the follow-through angle can be calculated using: 360°− vertical angle at the valley. For example, in FIG. 9B, the valley of the vertical angle θ (after the impact) is about 40°. Therefore, the follow-through angle is about 320°. Thus, the batter 100 almost swung the bat 102 in a complete circle from the 0° vertically downward position where the ball was hit.

Figure 9C:
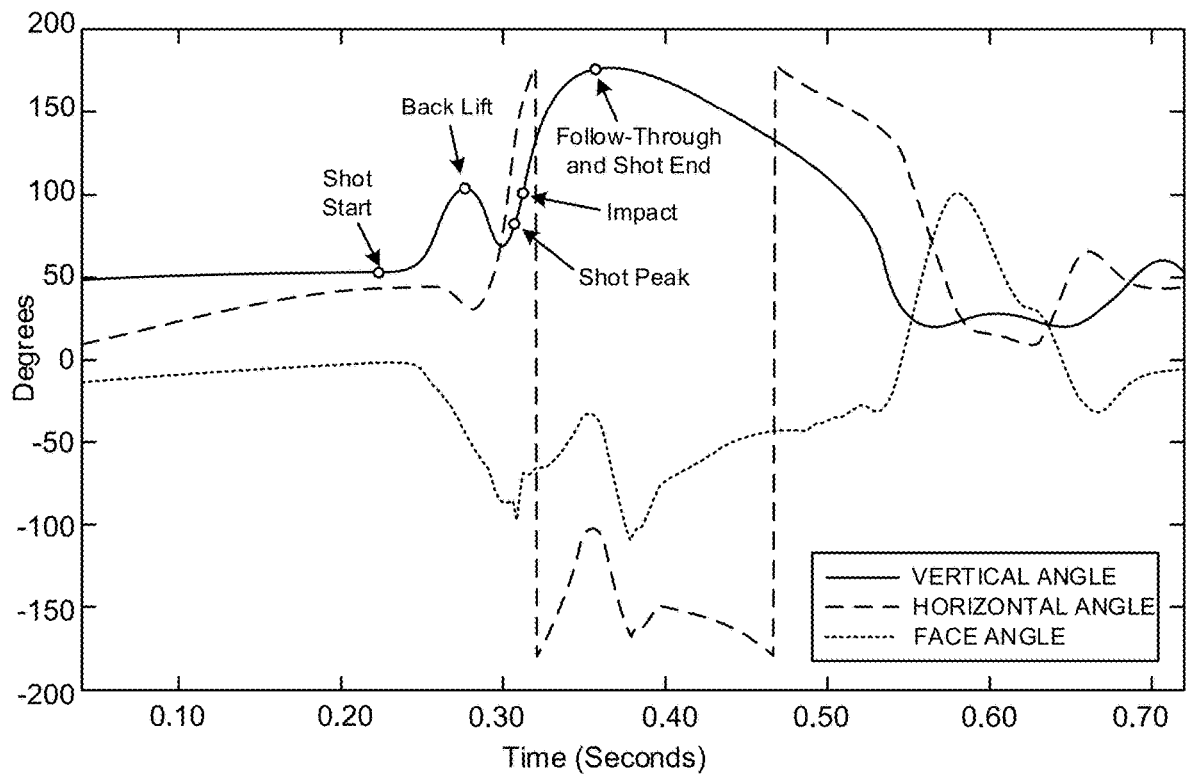
Figure 9D:
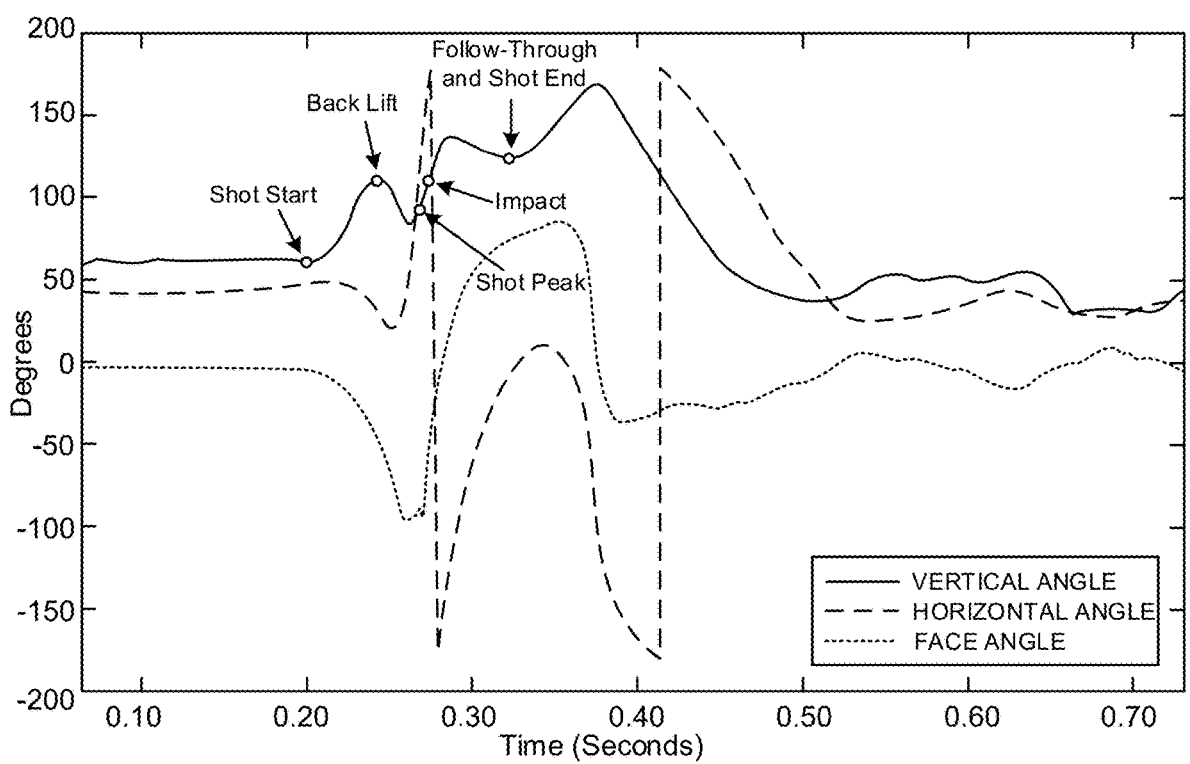

FIG. 9C is an example of an 'N' type curve of a horizontal shot. Similar to the graph of FIG. 9A, the vertical angle θ line forms one peak and one valley after the impact point (and before the magnitudes of the accelerometer 222 and the gyroscope 224 reach a minimum threshold). As such, the shot curve determiner 406 determines the swing follows an 'N' type curve. FIG. 9D is an example of an 'M' type curve of a horizontal shot. Similar to the graph of FIG. 9A, the vertical angle θ line forms two peaks and one valley after the impact point (and before the magnitudes of the accelerometer 222 and the gyroscope 224 reach a minimum threshold). As such, the shot curve determiner 406 determines the swing follows an 'M' type curve. While in the example graphs of FIGS. 9A-9D the horizontal angle 4 and the face angle φ are included, in other examples, the horizontal angle 4 and the face angle φ may not be calculated or graphed by the angle and orientation tracker 400.

Referring back to FIG. 4, the follow-through determiner 408 of the swing analyzer 230 determines the type of follow-through pattern and/or the follow-through angle based on the one or more metrics or parameters. For example, the follow-through determiner 408 may determine the type of follow-through pattern based on whether the shot is horizontal shot or vertical shot, whether the bat 102 went over the shoulder, and the type of curve ('N' or 'M') from vertical angle θ, as determined by the shot type determiner 402, the bat-over-shoulder determiner 404, and the shot curve determiner 406, respectively. Thus, the example follow-through determiner 408 determines the type of follow-through pattern based on movement data from the IMU 218.

In some examples, the follow-through determiner 408 determines the type of follow-through pattern from a set of follow-through patterns. For example, Table 1 below is an example table that may be used to identify the type of follow-through pattern based on various combinations of the metrics. The table may be stored in the database 410, for example. In Table 1, there are nine (9) types of follow-through patterns, numbered as Index Positions 1-9. However, in other examples, more or fewer follow-through patterns may be utilized based on different combinations of data. In Table 1, the first column indicates the Index Position or type of follow-through pattern, the second column indicates whether the swing was a vertical shot or a horizontal shot, the third column indicates whether the bat traveled over the batter's shoulder (Y) or not (N), the fourth column indicates whether the vertical angle followed an 'N' type or 'M' type curve, the fifth column indicates the number of peak(s) and valley(s) in the vertical angle after the impact point (and, in some examples, before the magnitudes of the accelerometer 222 and/or the gyroscope 224 are less than a threshold), and the sixth column represents the definition for determining the follow-through angle for the respective Index Position.

TABLE 1

| Index | Shot-Type | Over-the-Shoulder | N or M | Peak + Valley # | Follow-Through Angle Definition |
|---|---|---|---|---|---|
| 1 | Vertical | N | N | ≤2 | Vertical Angle Peak After Impact |
| 2 | Vertical | N | M | ≥3 | Second Vertical Angle Peak After Impact |
| 3 | Vertical | Y | N | 1 (last sample, no true peak found) | 360° - Vertical Angle Peak After Impact (which takes the maximum sample in vertical angle curve) |
| 4 | Vertical | Y | N | 1 (true peak) | 360° - Vertical Angle Valley After Impact (which takes the last minimum sample in vertical angle curve) |
| 5 | Vertical | Y | M | ≥2 | 360° - Vertical Angle Valley After Impact |
| 6 | Horizontal | N | N | ≤2 | Vertical Angle (After Impact) at Horizontal Angle Change Position |
| 7 | Horizontal | N | M | ≥3 | Vertical Angle (After Impact) at Horizontal Change Position |
| 8 | Horizontal | Y | N | 1 | 360° - Vertical Angle (After Impact) at Horizontal Change Position |
| 9 | Horizontal | Y | M | ≥2 | 360° - Vertical Angle Valley After Impact |

As shown in Table 1 above, each of the follow-through patterns is defined by a different combination of horizontal v. vertical, over-the-shoulder, 'N' v. 'M' type curves, and number of peaks and valleys after the impact positions. For example, if the swing is identified as a vertical shot (e.g., determined by the shot type determiner 402), the bat 102 does not travel over the shoulder of the batter 100 (e.g., determined by the bat-over-shoulder determiner 404), the vertical angle θ forms an 'N' type curve (e.g., determined by the shot curve determiner 406), and there is one peak and one valley (e.g., determined by the shot curve determiner 406) after the impact point, the follow-through determiner 408 determines the follow-through of the swing matches the pattern of Index Position 1. FIG. 9A is an example of a swing having the follow-through pattern of Index Position 1. As shown in FIG. 9A, there is one valley and one peak after the impact point. FIG. 9B is an example of a swing having the follow-through pattern of Index Position 5, FIG. 9C is an example of a swing having the follow-through pattern of Index Position 6, and FIG. 9D is an example of a swing having the follow-through pattern of Index Position 9. Thus, different combinations of these metrics may result in different follow-through patterns. In other words, each of the Index Positions represents a different follow-through pattern defined by a certain combination of the metrics.

Further, in some examples, the type of follow-through pattern can be used to identify the follow-through end point in the movement data and determine how to calculate the follow-through angle. For example, the sixth column in Table 1 includes a definition of how to calculate the follow-through angle (i.e., the angle of the bat 102 at the end of the follow-through stage) for each of the different types of follow-through patterns. For example, with the follow-through pattern of Index Position 1, the vertical angle peak after the impact point defines the follow-through, or ending position, angle. Therefore, referring back to FIG. 9A, the follow-through angle would correspond to the vertical angle at the peak (e.g., where the follow-through and shot end point is labeled), around 150°.

As another example, for the follow-through pattern of Index Position 5, the follow-through angle is defined by: 360°–the vertical angle valley after the impact point. For example, looking at FIG. 9B, the valley after the impact point is about 40°. Therefore, in this example, the follow-through angle is about 320°=360°–40°. Thus, the follow-through determiner 408 may calculate the follow-through angle using the associated definition from Table 1.

In some examples, the results of the swing analysis, including the type of follow-through pattern, the follow-through angle, the angle data (which may be used to show the angle graphs), etc. are transmitted (e.g., via the transceiver 220) to the electronic device 228. In some examples, the electronic device 228 uses the swing results to identify the key positions and/or stages of the swing, determine the angles and/or velocity of the bat at the key positions and/or stages of the swing, determine the time to impact (e.g., time between the back lift point and the impact point), determine whether or not there was impact (contact with the ball), and/or for bat path generation and shot reconstruction. In some examples, the swing results may be used to identify a type of shot, such square, pull, hook, and sweep, which are examples of horizontal type shots, or back foot punch, cover, lofted straight, straight, and flick, which are examples of vertical type shots. In some examples, the electronic device 228 may include a display screen that presents one or more of the results of the swing analysis to the batter 100 and/or another person. In some examples, presenting the results of the swing analysis can be used for training. For example, certain shot types may be preferred over other types of shots. A batter may learn what type of follow-through swing he/she is using. Further, some shot types have certain angle ranges. As such, a user may determine whether he/she is utilizing the full angle range of the shot type, which can help identify whether the player needs more practice or not. Additionally or alternatively, the results of the swing analysis may be presented to an audience. For example, this information may be broadcast on TV to an audience watching a cricket game after a batter swings, thereby providing the audience with enhanced data and information about the player's abilities.

While an example manner of implementing the swing analyzer 230 of FIG. 2 is illustrated in FIG. 4, one or more of the elements, processes and/or devices illustrated in FIG. 4 may be combined, divided, re-arranged, omitted, eliminated and/or implemented in any other way. Further, the example angle and orientation tracker 400, the example position determiner 401, the example shot type determiner 402, the example bat-over-shoulder determiner 404, the example shot curve determiner 406, the example follow-through determiner 408 and/or, more generally, the example swing analyzer 230 of FIG. 4 may be implemented by hardware, software, firmware and/or any combination of hardware, software and/or firmware. Thus, for example, any of the example angle and orientation tracker 400, the example position determiner 401, the example shot type determiner 402, the example bat-over-shoulder determiner 404, the example shot curve determiner 406, the example follow-through determiner 408 and/or, more generally, the example swing analyzer 230 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example angle and orientation tracker 400, the example position determiner 401, the example shot type determiner 402, the example bat-over-shoulder determiner 404, the example shot curve determiner 406, and/or the example follow-through determiner 408 is/are hereby expressly defined to include a non-transitory computer readable storage device or storage disk such as a memory, a digital versatile disk (DVD), a compact disk (CD), a Blu-ray disk, etc. including the software and/or firmware. Further still, the example swing analyzer of FIG. 4 may include one or more elements, processes and/or devices in addition to, or instead of, those illustrated in FIG. 4, and/or may include more than one of any or all of the illustrated elements, processes and devices.

Figure 10:
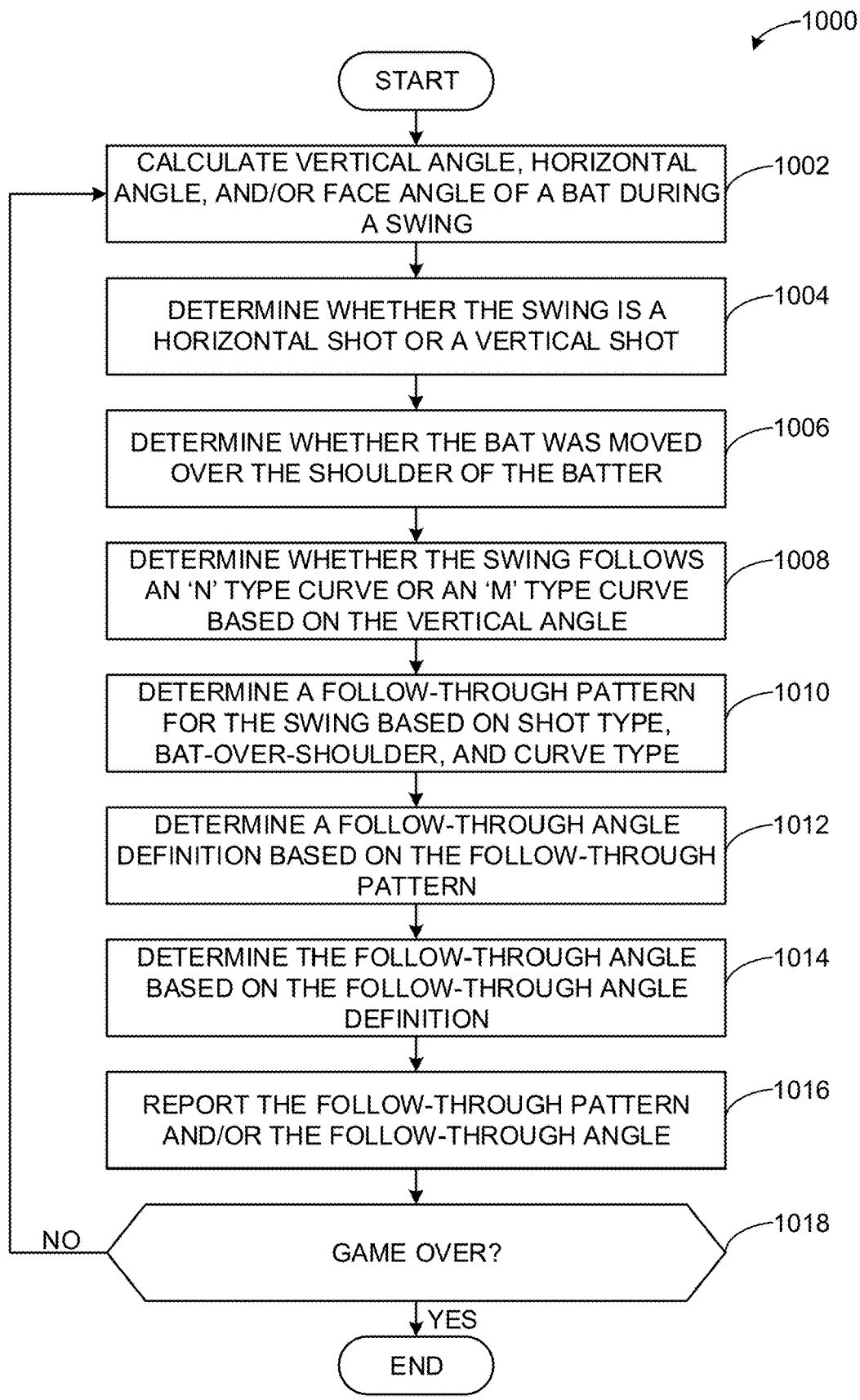
FIG. 10 is a flowchart representative of example machine readable instructions that may be executed to implement the example swing analyzer of FIG. 2 to determine a follow-through pattern and/or a follow-through angle of a swing of the example cricket bat.

A flowchart representative of example machine readable instructions for implementing the swing analyzer of FIG. 4 is shown in FIG. 10. In this example, the machine readable instructions comprise a program for execution by a processor such as the processor 1112 shown in the example processor platform 1100 discussed below in connection with FIG. 11. The program may be embodied in software stored on a non-transitory computer readable storage medium such as a CD-ROM, a floppy disk, a hard drive, a digital versatile disk (DVD), a Blu-ray disk, or a memory associated with the processor 1112, but the entire program and/or parts thereof could alternatively be executed by a device other than the processor 1112 and/or embodied in firmware or dedicated hardware. Further, although the example program is described with reference to the flowchart illustrated in FIG. 10, many other methods of implementing the example swing analyzer 230 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, a Field Programmable Gate Array (FPGA), an Application Specific Integrated circuit (ASIC), a comparator, an operational-amplifier (op-amp), a logic circuit, etc.) structured to perform the corresponding operation without executing software or firmware.

As mentioned above, the example processes of FIG. 10 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. "Including" and "comprising" (and all forms and tenses thereof) are used herein to be open ended terms. Thus, whenever a claim lists anything following any form of "include" or "comprise" (e.g., comprises, includes, comprising, including, etc.), it is to be understood that additional elements, terms, etc. may be present without falling outside the scope of the corresponding claim. As used herein, when the phrase "at least" is used as the transition term in a preamble of a claim, it is open-ended in the same manner as the term "comprising" and "including" are open ended.

FIG. 10 is a flowchart 1000 representative of example machine readable instructions that may be executed by the sensing unit 210 (e.g., via the microprocessor 216) to implement the example swing analyzer of FIG. 4. The example process of FIG. 10 is described in connection with the cricket bat 102. However, the example process of FIG. 10 may likewise be performed with any other sports implement, such as a baseball bat, a hockey stick, a golf club, etc.

At block 1002, the angle and orientation tracker 400 calculates the vertical angle $\theta$, the horizontal angle $\phi$, and/or the face angle $\varphi$ of the bat 102 during the swing. In some examples, the angle and orientation tracker 400 calculates the vertical angle $\theta$, the horizontal angle $\phi$, and/or the face angle $\varphi$ based on the movement data from the IMU 218, including measurements from the accelerometer 222, the gyroscope 224, and/or the magnetometer 226. In some examples, the angle(s) are calculated at a sampling rate of 100 HZ. In other examples, the angle(s) may be calculated at a higher or lower sampling rate. Therefore, the angle and orientation tracker 400 provides means for determining at least one of the vertical angle $\theta$, the horizontal angle $\phi$, or the face angle $\varphi$ of the bat 102 during a swing based on the movement data. In some examples, the position determiner 401 identifies the various key point(s) (e.g., shot start point, back lift point, etc.) and/or stage(s) (e.g., wind up, forward swing, follow-through, etc.) in the angle data based on the measurements from the IMU 218.

At block 1004, the shot type determiner 402 determines whether the swing is a horizontal shot or a vertical shot. In some examples, the shot type determiner 402 determines whether the swing is a horizontal shot or a vertical shot based on whether the change in vertical angle $\theta$ or horizontal angle $\phi$ is larger during the swing or a portion of the swing. In other examples, other techniques may be implemented by the shot type determiner 402. Therefore, the shot type determiner 402 provides means for determining whether the swing is a vertical shot or a horizontal shot.

At block 1006, the bat-over-shoulder determiner 404 determines whether the bat 102 was moved, during the follow-through stage, over the shoulder over the batter 100. In some examples, the bat-over-shoulder determiner 404 analyzes the angle and orientation data from the angle and orientation tracker 400 to determine the path of movement of the bat 102 during the follow-through. For example, referring briefly to FIG. 8, the bat-over-shoulder determiner 404 may determine the bat 102 was moved over the batter's shoulder if the bat 102 moves, during the follow-through, from Quadrant 2 into Quadrant 1, from Quadrant 3 into Quadrant 1, or from Quadrant 3 into Quadrant 4, based on the changes in horizontal angle ϕ. If the bat 102 does not move through the quadrants according to one of these criteria, the bat-over-shoulder determiner 404 determines the bat 102 did not move over the batter's shoulder during the follow-through stage. Therefore, the bat-over-shoulder determiner 404 provides means for determining whether the bat 102 traveled over a batter's shoulder.

At block 1008, the shot curve determiner 406 determines whether the swing follows an 'N' type curve or an 'M' type curve based on the shape of the vertical angle change throughout the swing. In some examples, the shot curve determiner 406 determines whether the swing follows an 'N' type curve or an 'M' type by identifying the number and/or positions of the peak(s) and valley(s) (i.e., minimums and maximums) of the vertical angle θ during the swing. For example, referring to FIGS. 9A-9D, the shot curve determiner 406 may analyze the vertical angle measurements to determine how many peaks and/or valleys are present and the position of the peaks and/or valleys relative to the different points and/or stages of the swing. A vertical angle θ having one peak and one valley (i.e., one maximum and one minimum) after the impact point may be considered an 'N' type curve, whereas a vertical angle θ having at least two peaks and one valley (i.e., two maximums and one minimum) after the impact point may be considered an 'M' type curve. Therefore, the shot curve determiner 406 provides means for identifying one or more peaks and valleys in the vertical angle θ and/or determining whether the bat 102 followed an 'N' type curve or an 'M' type curve.

At block 1010, the follow-through determiner 408 determines the type of follow-through pattern of the bat 102 based on whether the swing was a horizontal shot or a vertical shot (determined at block 1004), whether the bat 102 moved over the batter's shoulder during the follow-through (determined at block 1006), and whether the swing followed an 'N' type curve or an 'M' type curve (determined at block 1008). In some examples, the follow-through determiner 408 determines the type of follow-through pattern from a set of possible follow-through patterns, such as defined in Table 1 above. For example, as shown in Table 1, there are nine different follow-through patterns, representing a different combination of the results from the determinations at blocks 1004-1008. Thus, the follow-through determiner 408 provides means for determining a follow-through pattern of a swing based on movement data (e.g., acceleration measurement(s), gyroscope measurement(s), and/or magnetometer measurement(s)) obtained by the IMU 218.

At block 1012, the follow-through determiner 408 determines which follow-through angle definition should be used based on the follow-through pattern. For example, referring to Table 1 above, each follow-through pattern includes a definition of how to calculate the follow-through angle for the respective follow-through pattern. Further, in some examples, the definition may be used to by the position determiner 401 to determine the follow-through end point. At block 1014, the follow-through determiner 408 determines and/or calculates the follow-through angle of the swing using the follow-through angle definition for the identified follow-through pattern. Therefore, in some examples, the follow-through determiner 408 provides means for determining a definition for determining a follow-through angle of the bat 102 and/or means for determining the follow-through angle based on the definition.

At block 1016, swing analyzer 230 reports the identified/determined follow-through pattern (e.g., whether the swing was a horizontal shot or vertical shot, whether the bat 102 went over the shoulder, etc.), the follow-through angle, and/or any other data from the swing analysis. For example, the sensing unit 210 includes the transceiver 220 that can transmit the results to the electronic device 228. Therefore, in some examples, the transceiver 220 provides means for transmitting the results to the remote electronic device 228. In addition to or as an alternative to the follow-through pattern, the sensing unit 210 may transmit the angle data (e.g., the vertical angle θ, the horizontal angle ϕ, and/or the face angle φ), the position data, and/or any of the other measurements or metrics to the electronic device 228, which may be further processed and/or present the results (e.g., on a display screen, broadcast over TV, etc.).

At block 1018, the swing analyzer 230 determines whether the game is still being played and/or another swing is to be analyzed. If so, control returns to block 1002 and the swing analyzer 230 analyzes the next swing of the bat 102. If the game is over or the swing analyzer 230 is no longer needed (e.g., practice is over), the example process of FIG. 10 ends. In some examples, the swing analyzer 230 determines the game is still being played based on movement of the bat 102 (e.g., as detected by measurements from the IMU 218) within a threshold time (e.g., 5 minutes). If the bat 102 is not moved within the threshold time, the swing analyzer 230 may determine the game is over.

Figure 11:
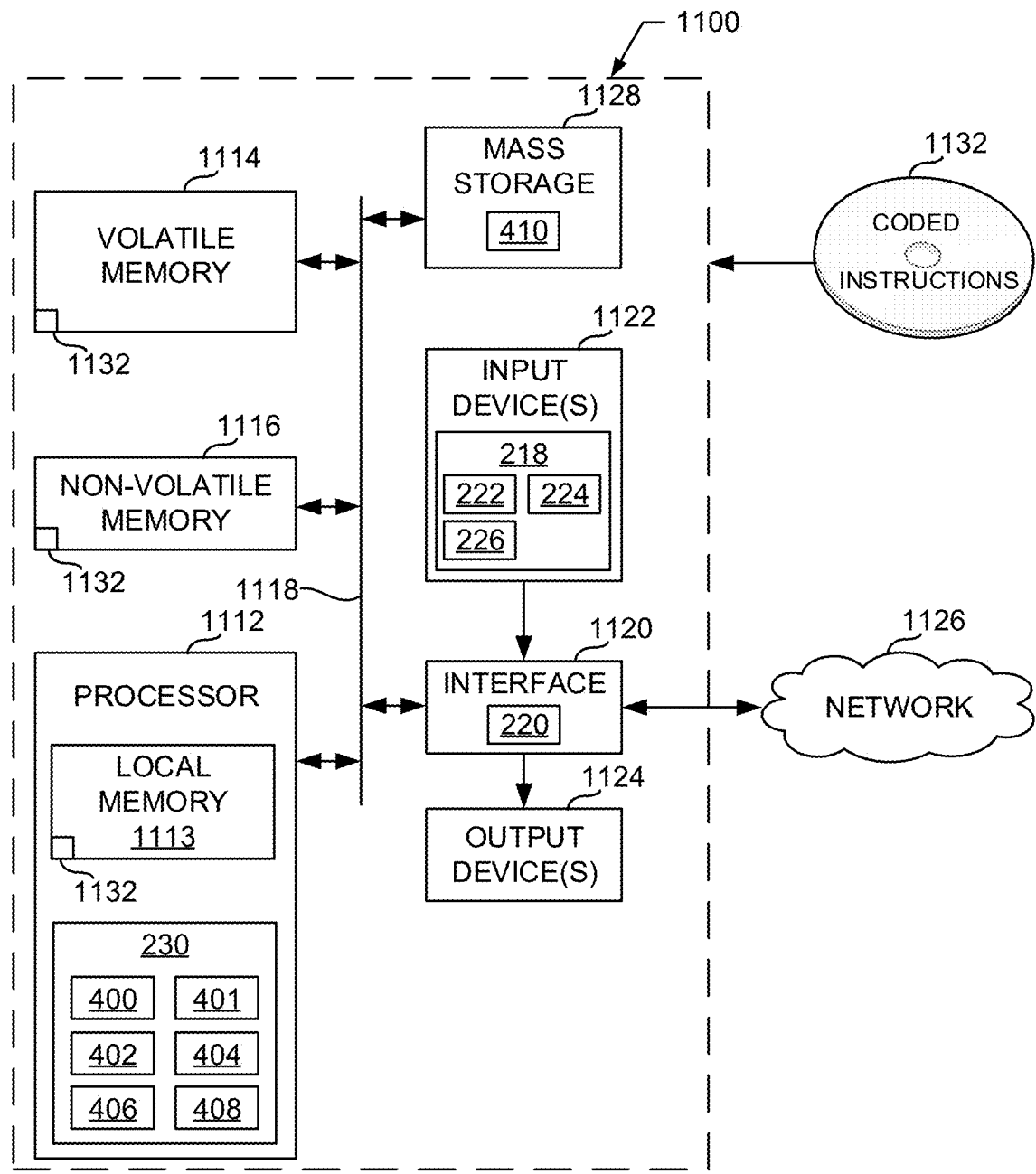
FIG. 11 is a processor platform that may execute the example instructions of FIG. 10 to implement the example swing analyzer of FIG. 2.

FIG. 11 is a block diagram of an example processor platform 1100 capable of executing the instructions of FIG. 10 to implement the swing analyzer 230 of FIG. 4. The processor platform 1100 may represent, for example, the sensing unit 210 of FIG. 2. In other examples, the processor platform 1100 may represent the electronic device 228 of FIG. 2, which can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, or any other type of computing device.

The processor platform 1100 of the illustrated example includes a processor 1112. The processor 1112 of the illustrated example is hardware. For example, the processor 1112 can be implemented by one or more integrated circuits, logic circuits, microprocessors or controllers from any desired family or manufacturer. The hardware processor may be a semiconductor based (e.g., silicon based) device. The processor 1112 may be, for example, the microprocessor 216 of FIG. 2. In this example, the processor 1112 implements the example angle and orientation tracker 400, the example position determiner 401, the example shot type determiner 402, the example bat-over-shoulder determiner 404, the example shot curve determiner 406, the example follow-through determiner 408 and/or, more generally, the example swing analyzer 230.

The processor 1112 of the illustrated example includes a local memory 1113 (e.g., a cache). The processor 1112 of the illustrated example is in communication with a main memory including a volatile memory 1114 and a non-volatile memory 1116 via a bus 1118. The volatile memory 1114 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1116 may be implemented by flash memory and/or any other desired type of memory device. Access to the main memory 1114, 1116 is controlled by a memory controller.

The processor platform 1100 of the illustrated example also includes an interface circuit 1120. The interface circuit 1120 may be implemented by any type of interface standard, such as an Ethernet interface, a universal serial bus (USB), and/or a PCI express interface. In this example, the interface circuit 1120 may include the transceiver 220.

In the illustrated example, one or more input devices 1122 are connected to the interface circuit 1120. The input device(s) 1122 permit(s) a user to enter data and/or commands into the processor 1112. The input device(s) can be implemented by, for example, an audio sensor, a microphone, a camera (still or video), a keyboard, a button, a mouse, a touchscreen, a track-pad, a trackball, isopoint and/or a voice recognition system. In this example, the input device(s) 1022 may include the IMU 218, including the accelerometer 222, the gyroscope 224, and/or the magnetometer 226.

One or more output devices 1124 are also connected to the interface circuit 1120 of the illustrated example. The output device(s) 1024 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 1120 of the illustrated example, thus, typically includes a graphics driver card, a graphics driver chip and/or a graphics driver processor.

The interface circuit 1120 of the illustrated example also includes a communication device such as a transmitter, a receiver, a transceiver, a modem and/or network interface card to facilitate exchange of data with external machines (e.g., computing devices of any kind) via a network 1126 (e.g., an Ethernet connection, a digital subscriber line (DSL), a telephone line, coaxial cable, a cellular telephone system, etc.).

The processor platform 1100 of the illustrated example also includes one or more mass storage devices 1128 for storing software and/or data. Examples of such mass storage devices 1128 include floppy disk drives, hard drive disks, compact disk drives, Blu-ray disk drives, RAID systems, and digital versatile disk (DVD) drives.

Coded instructions 1132 of FIG. 10 may be stored in the mass storage device 1128, in the volatile memory 1114, in the non-volatile memory 1116, and/or on a removable tangible computer readable storage medium such as a CD or DVD.

From the foregoing, it will be appreciated that example methods, apparatus, systems, and articles of manufacture have been disclosed that track movement of sports implements, such as a bat, and determine certain metrics about a follow-through pattern of a swing. Tracking the movement of a bat or other sports implement during a swing and, in particular, the follow-through stage, can be used for training the player, informative entertainment, etc. The examples disclosed herein provide a relatively simple, low-power sensing unit that may be used to analyze the movement of a sports implement during a swing and automatically report the results to be displayed and/or further processed. The example sensing units disclosed herein can be easily coupled to a bat and automatically report the swing results. Thus, the example sensing units do not require complex, expensive backend processors and additional infrastructure (e.g., cameras on a field) that are needed with known sports tracking systems.

Example methods, apparatus, systems, and/or articles of manufacture to track a sports bat are disclosed herein. Further examples and combinations thereof include the following:

Example 1 includes a sensing unit to be coupled to a sports implement. The sensing unit includes an inertial measurement unit to obtain movement data of said sports implement during a swing of said sports implement and a swing analyzer to determine a follow-through pattern of the swing of said sports implement based on the movement data.

Example 2 includes the sensing unit of Example 1, wherein the swing analyzer is to determine a follow-through angle of said sports implement based on the movement data. The follow-through angle corresponds to a vertical angle of said sports implement an end of a follow-through stage of the swing.

Example 3 includes the sensing unit of any of Examples 1 or 2, wherein the swing analyzer is to calculate at least one of a vertical angle, a horizontal angle, or a face angle of said sports implement during the swing based on the movement data, and wherein the swing analyzer is to determine the follow-through pattern based the at least one of the vertical angle, the horizontal angle and the face angle.

Example 4 includes the sensing unit of Example 3, wherein the swing analyzer is to identify one or more stages of the swing of said sports implement based on the at least one of the vertical angle, the horizontal angle and the face angle.

Example 5 includes the sensing unit of any of Examples 1 or 2, wherein the swing analyzer is to determine whether the swing is a horizontal shot or a vertical shot, and wherein the swing analyzer is to determine the follow-through pattern based on the determination of whether the swing of said sports implement is a horizontal shot or a vertical shot.

Example 6 includes the sensing unit of any of Examples 1 or 2, wherein the swing analyzer is to determine whether said sports implement traveled over a batter's shoulder during a follow-through stage of the swing, and wherein the swing analyzer is to determine the follow-through pattern based on the determination of whether said sports implement traveled over the batter's shoulder.

Example 7 includes the sensing unit of any of Examples 1 or 2, wherein the swing analyzer is to track a vertical angle of said sports implement during the swing, and wherein the swing analyzer is to determine the follow-through pattern based on a number of peaks and valleys in the vertical angle of the swing after an impact point.

Example 8 includes the sensing unit of any of Examples 1 or 2, wherein the inertial measurement unit includes at least one of an accelerometer, a gyroscope, or a magnetometer.

Example 9 includes the sensing unit of any of Examples 1 or 2, further including a power source.

Example 10 includes the sensing unit of any of Examples 1 or 2, further including a transceiver to transmit the follow-through pattern to a remote electronic device.

Example 11 includes a sports tracking system including a sensing unit coupled to a sports implement. The sensing unit includes an inertial measurement unit (IMU) to obtain movement data of the sports implement during a swing of the sports implement. The sports tracking system further includes a swing analyzer to determine a follow-through angle of the sports implement based on the movement data. The follow-through angle corresponds to a vertical angle of the sports implement an end of a follow-through stage of the swing.

Example 12 includes the sports tracking system of Example 11, wherein the sports implement is a cricket bat having a handle and a blade.

Example 13 includes the sports tracking system of Example 12, wherein the sensing unit is coupled to the cricket bat at or near an end of the handle.

Example 14 includes the sports tracking system of any of Examples 11-13, wherein the swing analyzer is implemented by a processor of the sensing unit.

Example 15 includes the sports tracking system of any of Examples 11-13, wherein the sensing unit includes a transmitter to transmit the follow-through angle of the sports implement to a remote electronic device.

Example 16 includes the sports tracking system of any of Examples 11-13, wherein the swing analyzer is implemented in a remote electronic device. The sensing unit includes a transceiver to transmit the movement data to the remote electronic device.

Example 17 includes the sports tracking system of any of Examples 11-13, wherein the sensing unit includes a battery.

Example 18 includes a non-transitory machine readable storage medium including instructions that, when executed, cause at least one machine to at least determine a follow-through pattern of a swing of a sports implement based on movement data obtained by an inertial measurement unit coupled to the sports implement.

Example 19 includes the non-transitory machine readable storage medium of Example 18, wherein the instructions, when executed, cause the at least one machine to determine a definition for determining a follow-through angle of the sports implement based on the follow-through pattern.

Example 20 includes the non-transitory machine readable storage medium of Example 19, wherein the instructions, when executed, cause the at least one machine to calculate the follow-through angle of the sports implement using the definition.

Example 21 includes the non-transitory machine readable storage medium of Example 19, wherein the instructions, when executed, cause the at least one machine to transmit the follow-through pattern and the follow-through angle to a remote electronic device.

Example 22 includes the non-transitory machine readable storage medium of any of Examples 18-21, wherein the instructions, when executed, cause the at least one machine to determine whether the swing is a vertical shot or a horizontal shot, and the instructions, when executed, cause the at least one machine to determine the follow-through pattern based on whether the swing is a vertical shot or a horizontal shot.

Example 23 includes the non-transitory machine readable storage medium of any of Examples 18-21, wherein the instructions, when executed, cause the at least one machine to determine if the sports implement traveled over a batter's shoulder during the swing, and the instructions, when executed, cause the at least one machine to determine the follow-through pattern based on whether the sports implement traveled over the batter's shoulder.

Example 24 includes the non-transitory machine readable storage medium of any of Examples 18-21, wherein the instructions, when executed, cause the at least one machine to determine a vertical angle of the sports implement during the swing based on the movement data, identify one or more peaks and valleys in the vertical angle of the sports implement after an impact point, and determine the follow-through pattern based on the identified number of peaks and valleys in the vertical angled.

Example 25 includes the non-transitory machine readable storage medium of any of Examples 18-21, wherein the sports implement is a cricket bat.

Example 26 includes an apparatus including means for determining a follow-through pattern of a swing of a sports implement based on movement data obtained by an inertial measurement unit coupled to the sports implement.

Example 27 includes the apparatus of Example 26, further including means for determining a definition for determining a follow-through angle of the sports implement based on the follow-through pattern.

Example 28 includes the apparatus of Example 27, further including means for determining the follow-through angle based on the definition.

Example 29 includes the apparatus of Example 27, further including means for transmitting the follow-through pattern and the follow-through angle to a remote electronic device.

Example 30 includes the apparatus of any of Examples 26-29, further including means for determining whether the swing is a vertical shot or a horizontal shot, and wherein the follow-through pattern is based on whether the swing is a vertical shot or a horizontal shot.

Example 31 includes the apparatus of any of Examples 26-29, further including means for determining whether the sports implement traveled over a batter's shoulder during the swing, and wherein the follow-through pattern is based on whether the sports implement traveled over the batter's shoulder.

Example 32 includes the apparatus of any of Examples 26-29, further including means for determining a vertical angle of the sports implement during the swing based on the movement data, and means for identifying one or more peaks and valleys in the vertical angle of the sports implement after an impact point, and wherein the follow-through pattern is based on the identified number of peaks and valleys in the vertical angle.

Example 33 includes the apparatus of any of Examples 26-29, wherein the sports implement is a cricket bat.

Although certain example methods, apparatus, systems and articles of manufacture have been disclosed herein, the scope of coverage of this patent is not limited thereto. On the contrary, this patent covers all methods, apparatus, systems and articles of manufacture fairly falling within the scope of the claims of this patent.

What is claimed is:

1. A sensing unit to be coupled to a sports implement, the sensing unit comprising:
   an inertial measurement unit to obtain movement data of said sports implement during a swing of said sports implement; and
   a swing analyzer to determine a follow-through pattern of the swing of said sports implement based on the movement data, the swing analyzer to determine the follow-through pattern by selecting a follow-through pattern from a plurality of predefined follow-though patterns, the plurality of predefined follow-through patterns based on (A) whether the swing of said sports implement is a horizontal shot or a vertical shot, (B) whether said sports implement travelled over a batter's shoulder during a follow-through stage of the swing, and (C) a number of peaks and valleys in a vertical angle of the swing of said sports implement after an impact point.

2. The sensing unit of claim 1, wherein the swing analyzer is to determine a follow-through angle of said sports implement based on the movement data, the follow-through angle corresponding to a vertical angle of said sports implement at an end of the follow-through stage of the swing.

3. The sensing unit of claim 2, further including a transmitter to transmit the determined follow-through pattern and the determined follow-through angle to a remote electronic device.

4. The sensing unit of claim 1, wherein the swing analyzer is to calculate at least one of a horizontal angle or a face angle of said sports implement during the swing based on the movement data, and wherein the swing analyzer is to determine the follow-through pattern based on the at least one of the horizontal angle or the face angle.

5. The sensing unit of claim 4, wherein the swing analyzer is to identify one or more stages of the swing of said sports implement based on the at least one of the vertical angle, the horizontal angle, or the face angle.

6. The sensing unit of claim 1, wherein the swing analyzer is to determine whether the swing of said sports implement is a horizontal shot or a vertical shot.

7. The sensing unit of claim 6, wherein the swing analyzer is to determine whether the swing of said sports implement is a horizontal shot or a vertical shot based on changes in horizontal angle and vertical angle of said sports implement during the swing.

8. The sensing unit of claim 6, wherein the swing analyzer is to determine whether the swing of said sports implement is a horizontal shot or a vertical shot based on a comparison of a change in vertical angle of said sports implement during the swing to a threshold.

9. The sensing unit of claim 1, wherein the swing analyzer is to determine whether said sports implement travelled over the batter's shoulder during the follow-through stage of the swing.

10. The sensing unit of claim 1, wherein the swing analyzer is to track the vertical angle of said sports implement during the swing.

11. The sensing unit of claim 1, wherein the inertial measurement unit includes at least one of an accelerometer, a gyroscope, or a magnetometer.

12. The sensing unit of claim 1, further including a transmitter to transmit the determined follow-through pattern to a remote electronic device.

13. A sports tracking system comprising:
a sensing unit coupled to a sports implement, the sensing unit including:
an inertial measurement unit (IMU) to obtain movement data of the sports implement during a swing of the sports implement; and
a swing analyzer to:
determine a follow-through pattern of the sports implement based on the movement data;
determine, based on the follow-through pattern, a definition for calculating a follow-through angle; and
calculate a follow-through angle of the sports implement using the definition, the follow-through angle corresponding to a vertical angle of the sports implement at an end of a follow-through stage of the swing; and
a transceiver to transmit the follow-through pattern and the follow-through angle to a remote electronic device.

14. The sports tracking system of claim 13, wherein the sports implement is a cricket bat having a handle and a blade.

15. The sports tracking system of claim 14, wherein the sensing unit is coupled to the cricket bat at or near an end of the handle.

16. The sports tracking system of claim 13, wherein the swing analyzer is implemented by a processor of the sensing unit.

17. A non-transitory machine readable storage medium comprising instructions that, when executed, cause at least one machine to at least:
determine a follow-through pattern of a swing of a sports implement based on movement data obtained by an inertial measurement unit coupled to the sports implement, wherein the follow-through pattern is determined from a plurality of predefined follow-through patterns, the plurality of predefined follow-through patterns based on different combinations of a plurality of metrics, wherein a different definition is associated with each of the predefined follow-through patterns for determining a follow-through angle associated with the respective follow-through pattern;
identify a definition associated with the determined follow-through pattern; and
calculate, using the identified definition, a follow-through angle of the sports implement.

18. The non-transitory machine readable storage medium of claim 17, wherein the instructions, when executed, cause the at least one machine to transmit the follow-through pattern and the follow-through angle to a remote electronic device.

19. The non-transitory machine readable storage medium of claim 17, wherein the instructions, when executed, cause the at least one machine to determine whether the swing is a vertical shot or a horizontal shot, and wherein one of the plurality of metrics is whether the swing is a vertical shot or a horizontal shot.

20. The non-transitory machine readable storage medium of claim 17, wherein the instructions, when executed, cause the at least one machine to determine if the sports implement traveled over a batter's shoulder during the swing, and wherein one of the plurality of metrics is whether the sports implement traveled over the batter's shoulder.

21. The non-transitory machine readable storage medium of claim 17, wherein the instructions, when executed, cause the at least one machine to:
determine a vertical angle of the sports implement during the swing based on the movement data; and
identify one or more peaks and valleys in the vertical angle of the sports implement after an impact point, wherein one of the plurality of metrics is based on the identified number of peaks and valleys in the vertical angle.

* * * * *